US00PP10534P

United States Patent [19]

Sjulin et al.

[11] Patent Number: Plant 10,534

[45] Date of Patent: Aug. 4, 1998

[54] STRAWBERRY PLANT NAMED 'LIDO'

[75] Inventors: Thomas M. Sjulin, Aromas; Amado Q. Amorao, Camarillo; Joseph I. Espejo, Jr., Watsonville; Joanne F. Coss, Salinas, all of Calif.

[73] Assignee: Driscoll Strawberry Associates, Inc., Watsonville, Calif.

[21] Appl. No.: 638,063

[22] Filed: Apr. 25, 1996

[51] Int. Cl.[6] ..... A01H 5/00

[52] U.S. Cl. ..... Plt./49

[58] Field of Search ..... Plt./48, 49

[56] References Cited

U.S. PATENT DOCUMENTS

P.P. 6,191 5/1988 Johnson et al. ..... Plt./48

OTHER PUBLICATIONS

UPOV ROM, disk 96/03, Results p. 1.

*Primary Examiner*—Howard J. Locker
*Assistant Examiner*—Kent L. Bell
*Attorney, Agent, or Firm*—Pennie & Edmonds LLP

[57] ABSTRACT

This invention relates to a new and distinct variety of strawberry plant named 'Lido', botanically identified as *Fragaria* × *ananassa*. The closest known variety is 'Swede'. The new variety is partially everbearing. The new variety is distinguished from 'Swede' by its glossier upper leaf surface, dense petiole pubescence and longer petiole pubescence. The cull rate for 'Lido' was 42% of that for 'Swede'. Following prolonged storage, the percent fruit that had rotted for 'Lido' was about 57% of that for 'Swede'. The reaction to disease was similar between 'Lido' and 'Swede', but 'Lido' is moderately resistant to Botrytis fruit rot, whereas 'Swede' is susceptible. The PGI isozyme banding pattern for 'Lido', is A3, while that for, 'Swede' is A1. The LAP and PGM banding patterns are B3 and C2, respectively, for both 'Lido' and 'Swede'.

4 Drawing Sheets

BACKGROUND OF THE INVENTION

The new variety of strawberry was discovered as a seedling in a controlled breeding plot in a cultivated area on the Fly Ranch near Pajaro, Monterey County, Calif., USA, in June, 1991. The seedling of the new variety was grow and asexually propagated by stolons in McArthur, Calif. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Lido'. Among the characteristics which distinguish the new variety from other varieties of which we are aware are a combination of traits which include stolon number, difference in shape between primary and secondary fruits, adherence of calyx, fruit firmness, and isozyme patterns.

Comparison to Closest Variety

The variety which we believe to be closest to 'Lido' from those known to us is 'Swede' (U.S. Plant Pat. No. 6,191). There are several characteristics of the new variety that are different from, or not possessed by 'Swede'. For example, the upper leaf surface of 'Lido' is glossier than that of 'Swede'. The petiole pubescence of 'Lido' is dense, while that of 'Swede' is medium. The petiole pubescence of 'Lido' is also longer than that of 'Swede'.

The cull rate for 'Lido' was 42% of that for 'Swede'. Following prolonged storage, the percent fruit that had rotted for 'Lido' was about 57% of that for 'Swede'. The reaction to disease is similar between 'Lido' and 'Swede', but 'Lido' is moderately resistant to Botrytis fruit rot, whereas 'Swede' is susceptible.

Regarding isozyme analysis, the PGI isozyme banding pattern for 'Lido' is A3, while that for 'Swede' is A1. The LAP and PGM banding patterns are B3 and C2, respectively, for both 'Lido' and 'Swede'. See J. Amer. Soc. Hort. Sci. 106: 684 (1981).

BRIEF DESCRIPTION OF THE ILLUSTRATIONS

The accompanying photographs show typical specimens of the new variety, including fruit, foliage and flower, in color as nearly true as it is reasonably possible to make in color illustrations of these characters.

DESCRIPTION OF THE NEW VARIETY

Figure 1:
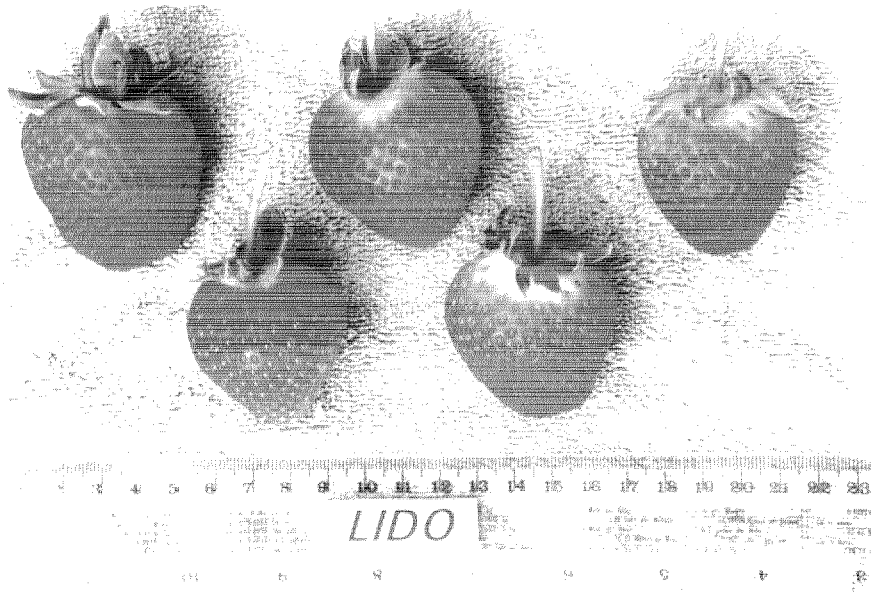
FIG. 1 shows typical whole fruit.
Figure 2:
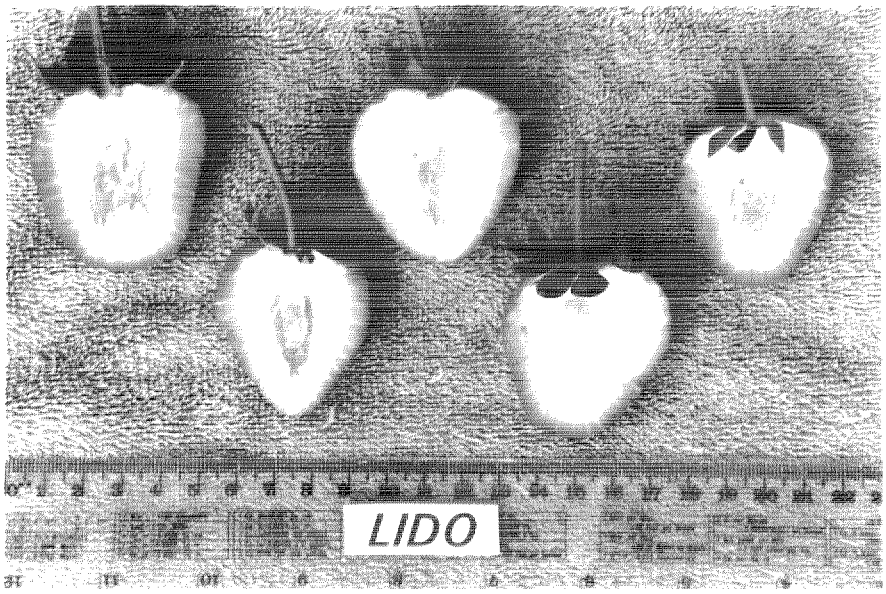
FIG. 2 shows the fruit in longitudinal section, illustrating the typical flesh and flesh coloration, conspicuous core and heart shape of the new variety.
Figure 3:
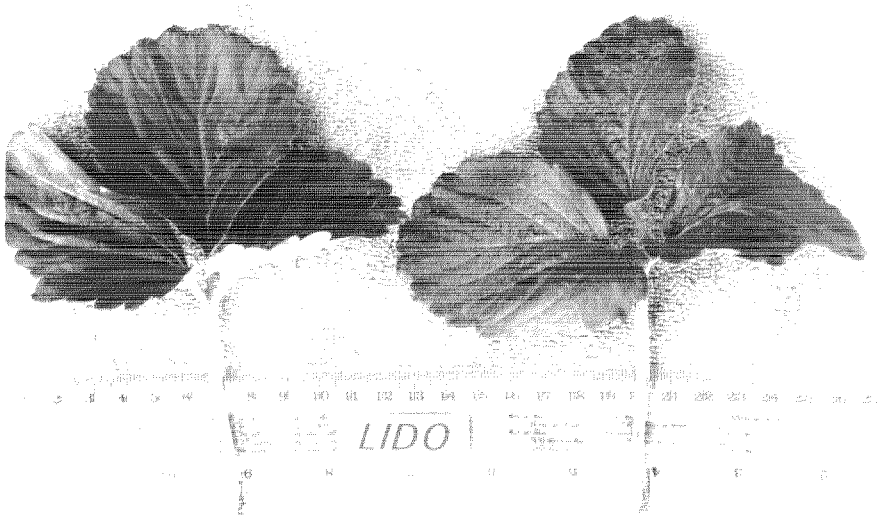
FIG. 3 shows the upper surface of two typical folioles of the new variety.
Figure 4:
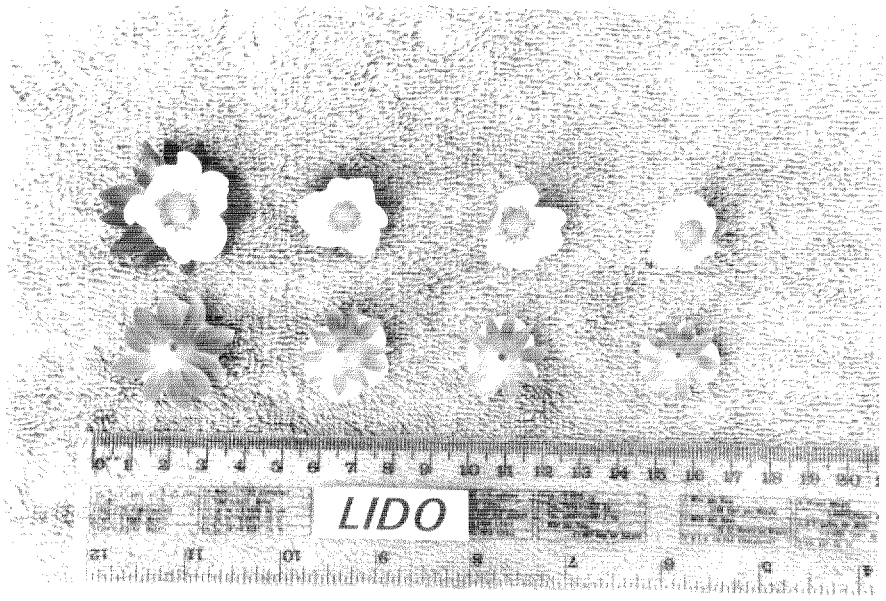
FIG. 4 shows the flower and reproductive organs of the new variety, as well as the size and position of the petals and sepals and the underside of the calyx.

The following detailed description of the new variety is based upon observations taken of plants and fruit grown in experimental test plots in Monterey County, Calif., U.S.A. in 1995. The strawberry varieties 'Swede' and 'Lido' were evaluated in a side-by-side comparison under similar conditions in a forcing system. In 1995, 'Lido' was first harvested the week of April 15. The last harvest occurred the week of October 28. These harvest dates are for the Smith Ranch in Salinas, Monterey County, Calif. This description is in accordance with UPOV terminology. Color designations, color descriptions, and other phenotypical descriptions may deviate from the stated values and descriptions depending upon variation in environmental, seasonal, climatic and cultural conditions.

Propagation

The new variety is principally propagated by way of stolons. Although propagation by stolons is presently preferred, other known methods of propagating strawberry plants may be employed. It has been determined that the plants root well after transplanting.

Characteristics of the New Variety

The following information is provided to describe the new variety.

Plant:

*Habit.*—Flat globose.

*Density.*—Medium to dense.

*Vigor.*—Weak.

Foliage:

*Leaf.*—Color—upperside—dark green, glossy. Profile (angle of leaf where attached to petiole)—concave. Blistering—medium to strong. Number of leaflets—three only.

*Terminal leaflet.*—Profile—revolute to flat. Length to width ratio—as long as broad. Shape of base—obtuse to rounded. Shape of teeth—rounded.

*Petiole.*—Pubescence—dense. Pose of hairs—outward.

*Stolons.*—Number—few. Anthocyanin coloration—medium. Thickness—thick. Pubescence—medium to dense.

*Inflorescence.*—Level with foliage.

Flower:

*Petal color.*—White; White is not referenced on the "Munsel Color Cascade".

*Size.*—Medium. 'Lido' has an average flower diameter of 27.2 mm, with a range from 20 to 34 mm.

*Diameter of calyx relative to corolla.*—Same size to larger.

*Diameter of inner calyx relative to outer (on secondary flowers).*—Same size.

*Spacing of petals (on secondary flowers with 5 or 6 petals).*—Overlapping.

*Petal length to width ratio (on secondary flowers).*—Broader than long to as long as broad.

*Fruiting truss.*—Attitude at first picking—semi-erect. Length—medium.

Fruit (secondary fruit on one year old plants):

*Ratio of length to maximum width.*—Broader than long to as long as broad.

*Size.*—Large.

*Predominant shape.*—Conical to cordate.

*Difference in shapes between primary and secondary fruits.*—Slight to moderate.

*Band without achenes.*—Absent or very narrow.

*Unevenness of surface.*—Medium.

*Skin color.*—Orange red

*Evenness of color.*—Even.

*Glossiness.*—Medium to strong.

*Insertion of achenes.*—Level with surface.

*Insertion of calyx.*—Level.

*Pose of the calyx segments.*—Reflexed.

*Size of calyx in relation to fruit diameter.*—Smaller.

*Adherence of calyx.*—Medium.

*Firmness of flesh (when fully ripe).*—Medium to firm.

*Color of flesh.*—Orange red.

*Evenness of color of flesh.*—Uneven.

*Sweetness.*—Medium to strong.

*Texture when tasted.*—Medium.

*Acidity.*—Weak to medium.

Time of flowering (50% of plants at first flower): Medium to late.

Harvest maturity (50% of plants with ripe fruit): Mid season.

Type of bearing: Partially everbearing. Partially everbearing varieties will continue to re-flower and fruit under cool conditions, such as those that occur in Coastal California. These varieties stop flowering under warm conditions.

Disease Resistance and Susceptibility

The 'Lido' variety is susceptible to *Xanthamonas fragariae, Verticillium wilt*, and the anthracnose disease caused by *Colletotrichum acutatum*. 'Lido' is moderately resistant to powdery mildew and aphid-borne virus diseases.

The 'Lido' strawberry fruit is moderately resistant to decay by *Botrytis cinerea* and Rhizopus spp.

The 'Lido' plant is susceptible to injury by the two spotted spider mite (*Tetranychus urticae*), cyclamen mite (*Phytonemus pallidus*), and lygus bug (*Lygus hesperus*).

What is claimed is:

1. A new and distinct variety of strawberry plant, substantially as shown and described.

* * * * *

1/4

3/4